(12) United States Patent
Barrus et al.

(10) Patent No.: US 9,566,167 B2
(45) Date of Patent: Feb. 14, 2017

(54) EXPANDABLE SPINAL IMPLANT

(71) Applicant: K2M, Inc., Leesburg, VA (US)

(72) Inventors: Michael Barrus, Ashburn, VA (US); Brandon Moore, Summit Point, WV (US)

(73) Assignee: K2M, Inc., Leesburg, VA (US)

( * ) Notice: Subject to any disclaimer, the term of this patent is extended or adjusted under 35 U.S.C. 154(b) by 0 days.

(21) Appl. No.: 14/466,303

(22) Filed: Aug. 22, 2014

(65) Prior Publication Data

US 2015/0057753 A1 Feb. 26, 2015

Related U.S. Application Data

(60) Provisional application No. 61/868,607, filed on Aug. 22, 2013.

(51) Int. Cl.
*A61F 2/44* (2006.01)
*A61F 2/46* (2006.01)
*A61F 2/30* (2006.01)

(52) U.S. Cl.
CPC ............ *A61F 2/4465* (2013.01); *A61F 2/4611* (2013.01); *A61F 2002/30492* (2013.01); *A61F 2002/30556* (2013.01); *A61F 2002/30601* (2013.01); *A61F 2002/30878* (2013.01)

(58) Field of Classification Search
CPC .................................................... A61F 2/4465
See application file for complete search history.

(56) References Cited

U.S. PATENT DOCUMENTS

| | | |
|---|---|---|
| 4,401,112 A | 8/1983 | Rezaian |
| 4,657,550 A | 4/1987 | Daher |
| 5,290,312 A | 3/1994 | Kojimoto et al. |
| 5,571,192 A | 11/1996 | Schonhoffer |
| 5,702,455 A | 12/1997 | Saggar |
| 5,865,848 A | 2/1999 | Baker |
| 5,916,267 A | 6/1999 | Tienboon |
| 5,989,290 A | 11/1999 | Biedermann et al. |
| 6,015,436 A | 1/2000 | Schonhoffer |
| 6,174,334 B1 | 1/2001 | Suddaby |
| 6,176,881 B1 | 1/2001 | Schar et al. |
| 6,190,413 B1 | 2/2001 | Sutcliffe |
| 6,193,755 B1 | 2/2001 | Metz-Stavenhagen et al. |

(Continued)

FOREIGN PATENT DOCUMENTS

SU 1560184 A1 4/1990

*Primary Examiner* — Jan Christopher Merene
(74) *Attorney, Agent, or Firm* — Carter, DeLuca, Farrell & Schmidt, LLP (57) ABSTRACT

An expandable spinal implant configured for positioning within a space between adjacent vertebral bodies includes an upper body, a lower body, and first and second pins. The lower body is adapted to slidably receive the upper body. Grooves are disposed on opposing side surfaces of the upper body, and grooves are disposed on an inner surface of a bore defined through the lower body. Corresponding first and second apertures are defined through an end surface of the lower body thereby permitting advancement of the first and second pins within the first and second apertures, grooves of the lower body, and a corresponding pair of grooves of the upper body to secure the position of the upper body relative to the lower body. A method of performing spinal surgery is also disclosed.

10 Claims, 8 Drawing Sheets

(56) References Cited

U.S. PATENT DOCUMENTS

| | | |
|---|---|---|
| 6,193,756 B1 | 2/2001 | Studer et al. |
| 6,200,348 B1 | 3/2001 | Biedermann et al. |
| 6,214,050 B1 | 4/2001 | Huene |
| 6,296,665 B1 | 10/2001 | Strnad et al. |
| 6,332,895 B1 | 12/2001 | Suddaby |
| 6,344,057 B1 | 2/2002 | Rabbe et al. |
| 6,352,556 B1 | 3/2002 | Kretschmer et al. |
| 6,375,683 B1 | 4/2002 | Crozet et al. |
| 6,395,034 B1 | 5/2002 | Suddaby |
| 6,409,766 B1 | 6/2002 | Brett |
| 6,419,705 B1 | 7/2002 | Erickson |
| 6,454,806 B1 | 9/2002 | Cohen et al. |
| 6,524,341 B2 | 2/2003 | Lang et al. |
| 6,562,074 B2 | 5/2003 | Gerbec et al. |
| 6,610,090 B1 | 8/2003 | Bohm et al. |
| 6,616,695 B1 | 9/2003 | Crozet et al. |
| 6,783,547 B2 | 8/2004 | Castro |
| 6,866,682 B1 | 3/2005 | An et al. |
| 6,902,579 B2 | 6/2005 | Harms et al. |
| 7,018,415 B1 | 3/2006 | McKay |
| 7,029,498 B2 | 4/2006 | Boehm et al. |
| 7,056,343 B2 | 6/2006 | Schafer et al. |
| 7,094,257 B2 | 8/2006 | Mujwid et al. |
| 7,156,874 B2 | 1/2007 | Paponneau et al. |
| 7,211,112 B2 | 5/2007 | Baynham et al. |
| 7,311,733 B2 | 12/2007 | Metz-Stavenhagen |
| 7,458,988 B2 | 12/2008 | Trieu et al. |
| 7,544,208 B1 | 6/2009 | Mueller et al. |
| 7,547,325 B2 | 6/2009 | Biedermann et al. |
| 7,575,601 B2 | 8/2009 | Dickson |
| 7,588,573 B2 | 9/2009 | Berry |
| 7,615,078 B2 | 11/2009 | White et al. |
| 7,618,458 B2 | 11/2009 | Biedermann et al. |
| 7,621,953 B2 | 11/2009 | Braddock, Jr. et al. |
| 7,641,693 B2 | 1/2010 | Gutlin et al. |
| 7,674,296 B2 | 3/2010 | Rhoda et al. |
| 7,691,147 B2 | 4/2010 | Gutlin et al. |
| 7,708,779 B2 | 5/2010 | Edie |
| 7,731,752 B2 | 6/2010 | Edie et al. |
| 7,744,650 B2 | 6/2010 | Lindner et al. |
| 7,758,648 B2 | 7/2010 | Castleman et al. |
| 7,794,501 B2 | 9/2010 | Edie et al. |
| 7,803,191 B2 | 9/2010 | Biedermann et al. |
| 7,815,683 B2 | 10/2010 | Melkent et al. |
| 7,819,920 B2 | 10/2010 | Assaker |
| 7,819,922 B2 | 10/2010 | Sweeney |
| 7,828,849 B2 | 11/2010 | Lim |
| 7,850,733 B2 | 12/2010 | Baynham et al. |
| 7,862,618 B2 | 1/2011 | White et al. |
| 7,883,542 B2 | 2/2011 | Zipnick |
| 7,887,596 B2 | 2/2011 | Douget et al. |
| 7,909,870 B2 | 3/2011 | Kraus |
| 7,914,581 B2 | 3/2011 | Dickson et al. |
| 7,967,867 B2 | 6/2011 | Barreiro et al. |
| 7,981,157 B2 | 7/2011 | Castleman et al. |
| 8,034,111 B2 | 10/2011 | Hsu et al. |
| 8,062,366 B2 | 11/2011 | Melkent |
| 8,062,368 B2 | 11/2011 | Heinz et al. |
| 8,062,375 B2 | 11/2011 | Glerum et al. |
| 8,070,817 B2 | 12/2011 | Gradl et al. |
| 8,105,382 B2 | 1/2012 | Olmos et al. |
| 8,110,004 B2 | 2/2012 | Valdevit et al. |
| 8,123,809 B2 | 2/2012 | Melkent et al. |
| 8,128,701 B2 | 3/2012 | Kast |
| 8,133,232 B2 | 3/2012 | Levy et al. |
| 8,152,852 B2 | 4/2012 | Biyani |
| 8,157,864 B2 | 4/2012 | Rogeau et al. |
| 8,163,020 B2 | 4/2012 | Le Huec |
| 8,177,846 B2 | 5/2012 | Blackwell et al. |
| 8,182,535 B2 | 5/2012 | Kraus |
| 8,182,537 B2 | 5/2012 | Refai et al. |
| 8,187,328 B2 | 5/2012 | Melkent |
| 8,187,331 B2 | 5/2012 | Strohkirch, Jr. et al. |
| 8,197,546 B2 | 6/2012 | Doubler et al. |
| 8,202,321 B2 | 6/2012 | Gerner |
| 8,211,178 B2 | 7/2012 | Melkent et al. |
| 8,241,294 B2 | 8/2012 | Sommerich et al. |
| 8,241,358 B2 | 8/2012 | Butler et al. |
| 8,241,363 B2 | 8/2012 | Sommerich et al. |
| 8,252,054 B2 | 8/2012 | Greenhalgh et al. |
| 8,267,939 B2 | 9/2012 | Cipoletti et al. |
| 8,268,002 B2 | 9/2012 | Blackwell et al. |
| 8,268,004 B2 | 9/2012 | Castleman et al. |
| 8,273,124 B2 | 9/2012 | Renganath et al. |
| 8,273,126 B2 | 9/2012 | Lindner |
| 8,292,963 B2 | 10/2012 | Miller et al. |
| 8,308,802 B2 | 11/2012 | Rhoda et al. |
| 8,317,866 B2 | 11/2012 | Palmatier et al. |
| 8,328,871 B2 | 12/2012 | Capote et al. |
| 8,337,558 B2 | 12/2012 | Lindner |
| 8,353,963 B2 | 1/2013 | Glerum |
| 8,366,777 B2 | 2/2013 | Matthis et al. |
| 8,377,140 B2 | 2/2013 | DeFalco et al. |
| 8,382,842 B2 | 2/2013 | Greenhalgh et al. |
| 8,398,713 B2 | 3/2013 | Weiman |
| 8,409,283 B2 | 4/2013 | Drochner et al. |
| 8,425,608 B2 | 4/2013 | Dewey et al. |
| 8,425,611 B2 | 4/2013 | Dewey et al. |
| 8,535,380 B2 | 9/2013 | Greenhalgh et al. |
| 8,540,770 B2 | 9/2013 | Woodburn, Sr. et al. |
| 8,551,173 B2 | 10/2013 | Lechmann et al. |
| 8,574,300 B2 | 11/2013 | McManus et al. |
| 8,585,763 B2 | 11/2013 | Olevsky et al. |
| 8,591,585 B2 | 11/2013 | McLaughlin et al. |
| 8,628,578 B2 | 1/2014 | Miller et al. |
| 8,657,882 B2 | 2/2014 | Bonin, Jr. |
| 8,663,329 B2 | 3/2014 | Ernst |
| 8,679,183 B2 | 3/2014 | Glerum et al. |
| 8,740,980 B2 | 6/2014 | Merves |
| 8,876,905 B2 | 11/2014 | Frasier |
| 2001/0039456 A1 | 11/2001 | Boyer et al. |
| 2004/0087947 A1 | 5/2004 | Lim et al. |
| 2004/0186569 A1 | 9/2004 | Berry |
| 2004/0210312 A1 | 10/2004 | Neumann |
| 2004/0215191 A1* | 10/2004 | Kitchen ............ A61B 17/7002 606/254 |
| 2005/0060036 A1 | 3/2005 | Schultz et al. |
| 2005/0283245 A1 | 12/2005 | Gordon et al. |
| 2006/0058879 A1 | 3/2006 | Metz-Stavenhagen |
| 2006/0167547 A1 | 7/2006 | Suddaby |
| 2006/0167548 A1* | 7/2006 | Jackson ............... A61F 2/4455 623/17.11 |
| 2007/0123987 A1 | 5/2007 | Bernstein |
| 2007/0270964 A1* | 11/2007 | Strohkirch, Jr. .......... A61F 2/44 623/17.11 |
| 2008/0021559 A1 | 1/2008 | Thramann |
| 2008/0058930 A1* | 3/2008 | Edie ..................... A61F 2/44 623/17.11 |
| 2008/0058931 A1 | 3/2008 | White et al. |
| 2008/0114467 A1* | 5/2008 | Capote ..................... A61F 2/44 623/23.47 |
| 2008/0161933 A1 | 7/2008 | Grotz et al. |
| 2008/0167720 A1 | 7/2008 | Melkent |
| 2008/0177387 A1 | 7/2008 | Parimore et al. |
| 2008/0243254 A1 | 10/2008 | Butler |
| 2008/0281424 A1 | 11/2008 | Parry et al. |
| 2008/0288071 A1 | 11/2008 | Biyani et al. |
| 2009/0112325 A1 | 4/2009 | Refai et al. |
| 2009/0216331 A1 | 8/2009 | Grotz et al. |
| 2009/0281625 A1 | 11/2009 | Enayati |
| 2010/0016969 A1 | 1/2010 | Richter et al. |
| 2010/0082106 A1 | 4/2010 | Muhanna |
| 2010/0082109 A1 | 4/2010 | Greenhalgh et al. |
| 2010/0094424 A1 | 4/2010 | Woodburn et al. |
| 2010/0145455 A1 | 6/2010 | Simpson et al. |
| 2010/0191336 A1 | 7/2010 | Greenhalgh |
| 2010/0249846 A1* | 9/2010 | Simonson ........... A61B 17/7037 606/264 |
| 2011/0015741 A1 | 1/2011 | Melkent et al. |
| 2011/0035009 A1 | 2/2011 | Sweeney |
| 2011/0138948 A1 | 6/2011 | Jimenez et al. |
| 2011/0184524 A1 | 7/2011 | Wiedenbeck et al. |
| 2011/0190890 A1 | 8/2011 | Blackwell et al. |
| 2011/0251692 A1 | 10/2011 | McLaughlin et al. |

(56) References Cited

U.S. PATENT DOCUMENTS

| | | |
|---|---|---|
| 2011/0264220 A1 | 10/2011 | Miller |
| 2012/0016476 A1 | 1/2012 | Wilfong et al. |
| 2012/0016478 A1 | 1/2012 | Wilfong et al. |
| 2012/0029635 A1 | 2/2012 | Schoenhoeffer et al. |
| 2012/0029638 A1 | 2/2012 | Miller et al. |
| 2012/0029640 A1 | 2/2012 | Capote et al. |
| 2012/0071977 A1 | 3/2012 | Oglaza et al. |
| 2012/0109302 A1 | 5/2012 | Miller et al. |
| 2012/0109307 A1 | 5/2012 | Drochner et al. |
| 2012/0197398 A1 | 8/2012 | Miller et al. |
| 2012/0209384 A1 | 8/2012 | Arnold et al. |
| 2012/0226356 A1 | 9/2012 | Hirschl |
| 2012/0232660 A1 | 9/2012 | Davenport |
| 2012/0330421 A1 | 12/2012 | Weiman |
| 2013/0103156 A1 | 4/2013 | Packer et al. |
| 2013/0116791 A1 | 5/2013 | Theofilos |
| 2013/0197648 A1 | 8/2013 | Boehm et al. |
| 2013/0211526 A1 | 8/2013 | Alheidt et al. |
| 2014/0142706 A1 | 5/2014 | Hansell et al. |

\* cited by examiner

EXPANDABLE SPINAL IMPLANT

CROSS-REFERENCE TO RELATED APPLICATION

This application claims priority to, and the benefit of, U.S. Provisional Patent Application Ser. No. 61/868,607, filed on Aug. 22, 2013, the entire contents of which are incorporated by reference herein.

TECHNICAL FIELD

The present disclosure relates generally to devices and methods for treating spinal conditions, and in particular, to expandable spinal implants configured for positioning within an intervertebral space.

BACKGROUND

The human spine includes thirty-three vertebrae. The vertebrae interlock with one another to form a spinal column. Each vertebra has a cylindrical bony body (vertebral body), two pedicles extending from the vertebral body, a lamina extending from the pedicles, two wing-like projections extending from the pedicles, a spinous process extending from the lamina, a pars interarticularis, two superior facets extending from the pedicles, and two inferior facets extending from the lamina. The vertebrae are separated and cushioned by thin pads of tough, resilient fiber known as intervertebral discs. Intervertebral discs provide flexibility to the spine and act as shock absorbers during activity. A small opening (foramen) located between each vertebra allows passage of nerves. When the vertebrae are properly aligned, the nerves pass through without a problem. However, when the vertebrae are misaligned or a constriction is formed in the spinal canal, the nerves get compressed and may cause back pain, leg pain, or other neurological disorders.

Disorders of the spine that may cause misalignment of the vertebrae or constriction of the spinal canal include spinal injuries, infections, tumor formation, herniation of the intervertebral discs (i.e., slippage or protrusion), arthritic disorders, and scoliosis. In these pathologic circumstances, surgery may be tried to either decompress the neural elements and/or fuse adjacent vertebral segments. Decompression may involve laminectomy, discectomy, or corpectomy. Laminectomy involves the removal of part of the lamina, i.e., the bony roof of the spinal canal. Discectomy involves removal of the intervertebral discs. Corpectomy involves removal of the vertebral body as well as the adjacent intervertebral discs.

The time-honored method of addressing the issues of neural irritation and instability resulting from severe disc damage have largely focused on removal of the damaged disc and fusing the adjacent vertebral elements together. Removal of the disc relieves the mechanical and chemical irritation of neural elements, while osseous union (bone knitting) solves the problem of instability.

While cancellous bone appears ideal to provide the biologic components necessary for osseous union to occur, it does not initially have the strength to resist the tremendous forces that may occur in the intervertebral disc space, nor does it have the capacity to adequately stabilize the spine until long term bony union occurs. For these reasons, many spinal surgeons have found that interbody fusion using bone alone has an unacceptably high rate of bone graft migration, expulsion, or nonunion due to structural failures of the bone or residual degrees of motion that retard or prohibit bony union. Therefore, intervertebral prostheses in various forms have been used to provide immediate stability and to protect and preserve an environment that fosters growth of grafted bone such that a structurally significant bony fusion can occur.

Many intervertebral implants have one or more fixed dimensions that may create challenges and/or lead to compromises when selecting a suitable implant for a surgical procedure.

Therefore, a need exists for an expandable spinal implant that can be inserted in a collapsed state in order to prevent over retraction of the anatomy, a reduction in surgical morbidity, and/or substandard implant sizing. Once the expandable spinal implant is in place, it can then be expanded to fill the anatomical space appropriately.

SUMMARY

The present disclosure relates to expandable spinal implants configured for positioning within an intervertebral space. The spinal implant includes an upper body, a lower body, and first and second pins. The upper body includes an outer surface adapted to engage a first vertebral body, and grooves disposed on opposing side surfaces. The lower body includes an outer surface adapted to engage a second, opposing, vertebral body, and a bore to slidably receive a portion of the upper body. The bore includes grooves disposed on opposing sides of an inner surface of the bore, and first and second apertures extending through an end surface of the lower body. First and second pins are adapted to be received within the first and second apertures, grooves of the lower body, and the grooves of the upper body to enable the first and second pins to secure a position of the upper body relative to the lower body.

In aspects, the spinal implant includes a cut-out defined through the outer surface and an opposing surface of the upper body.

In aspects, the outer surfaces of each of the upper body and the lower body include ridges adapted to engage the first and second vertebral bodies.

In aspects, a through-hole is defined through a side surface of the lower body. The through-hole is configured to engage an insertion instrument capable of inserting the spinal implant between adjacent vertebral bodies.

In aspects, a slot is defined through a side surface of the upper body. The slot is configured to slidably engage an insertion instrument such that the upper body may advance axially in the bore of the lower body.

In aspects, the grooves of the upper body are disposed in a stacked orientation.

In aspects, the upper body includes a flange disposed on the outer surface adapted to abut the opposing surface of the lower body.

A method of performing surgery is also disclosed. The method includes providing a spinal implant including an upper body, a lower body, and first and second pins. The upper body includes an outer surface adapted to engage a first vertebral body, and grooves disposed on opposing side surfaces. The lower body includes an outer surface adapted to engage a second, opposing, vertebral body, and a bore to slidably receive a portion of the upper body. The bore includes grooves disposed on opposing sides of an inner surface of the bore, and first and second apertures extending through an end surface of the lower body. First and second pins are adapted to be received within the first and second apertures, grooves of the lower body, and the grooves of the upper body to enable the first and second pins to secure a position of the upper body relative to the lower body. The method further includes inserting the upper body within the bore of the lower body, preparing an intervertebral space between first and second vertebral bodies to receive the spinal implant, inserting the spinal implant into the prepared intervertebral space, expanding the spinal implant to obtain a desired height, and inserting the first and second pins into the first and second apertures, grooves of the lower body, and a corresponding pair of grooves of the upper body, thereby securing the position of the upper body relative to the lower body at the desired height of the spinal implant.

In aspects, inserting the spinal implant includes first securing the spinal implant to an insertion device.

In aspects, the method further includes packing a cut-out defined through the outer surface and an opposing surface of the upper body with bone in-growth material.

In aspects, the method further includes packing a cut-out defined through the outer surface and an opposing surface of the upper body with drugs.

In aspects, expanding the spinal implant includes advancing the upper body axially in the bore of the lower body.

In aspects, expanding the spinal implant includes positioning the upper body and lower body in a desired position relative to each other.

In aspects, inserting the spinal implant includes inserting the spinal implant within the prepared intervertebral space from an anterior approach, an anteriolateral approach, a lateral approach, a retro-peritoneal approach, or a posterior approach.

In aspects, expanding the spinal implant includes expanding the spinal implant manually.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiments given below, serve to explain the principles of the disclosure, wherein.

DETAILED DESCRIPTION

Embodiments of the present disclosure are now described in detail with reference to the drawings in which like reference numerals designate identical or corresponding elements in each of the several views. As used herein, the term "clinician" refers to a doctor, a nurse or any other care provider and may include support personnel. Throughout this description, the term "proximal" will refer to the portion of the device or component thereof that is closer to the clinician and the term "distal" will refer to the portion of the device or component thereof that is farther from the clinician. Additionally, in the drawings and in the description that follows, terms such as front, rear, upper, lower, top, bottom, and similar directional terms are used simply for convenience of description and are not intended to limit the disclosure. In the following description, well-known functions or constructions are not described in detail to avoid obscuring the present disclosure in unnecessary detail.

Figure 1:
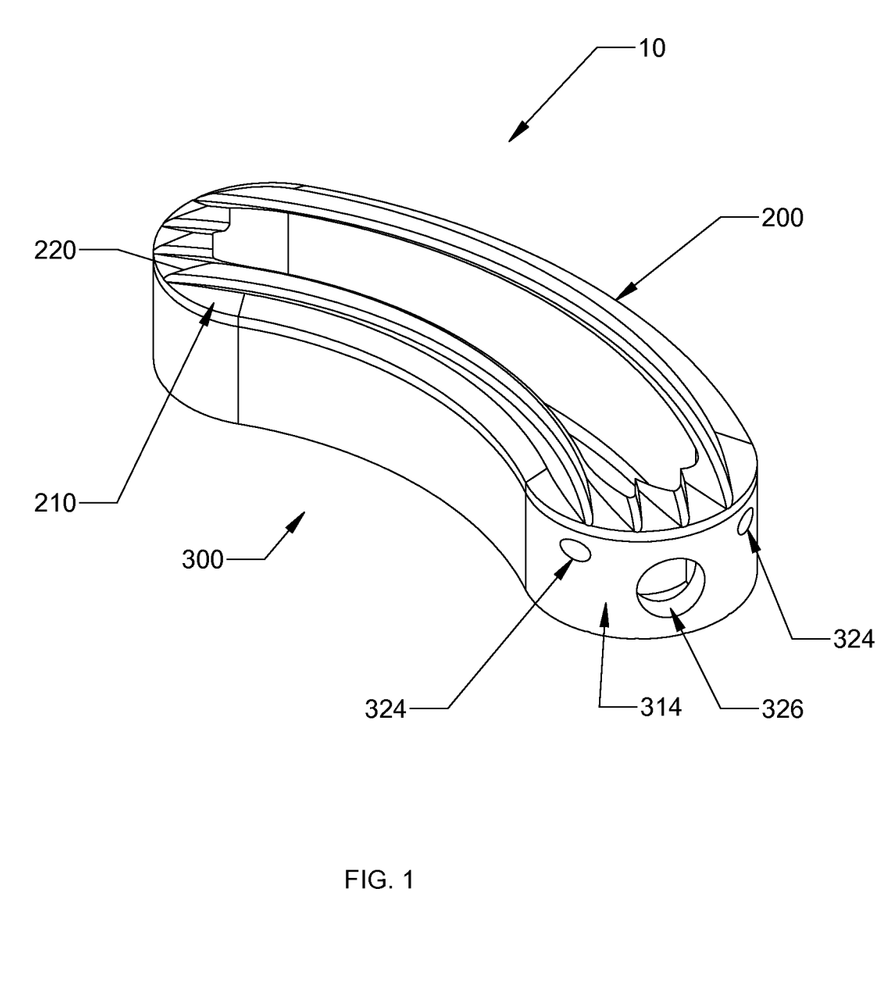
FIG. 1 is a perspective view of an expandable spinal implant provided in accordance with the present disclosure, shown in a collapsed state.
Figure 5:
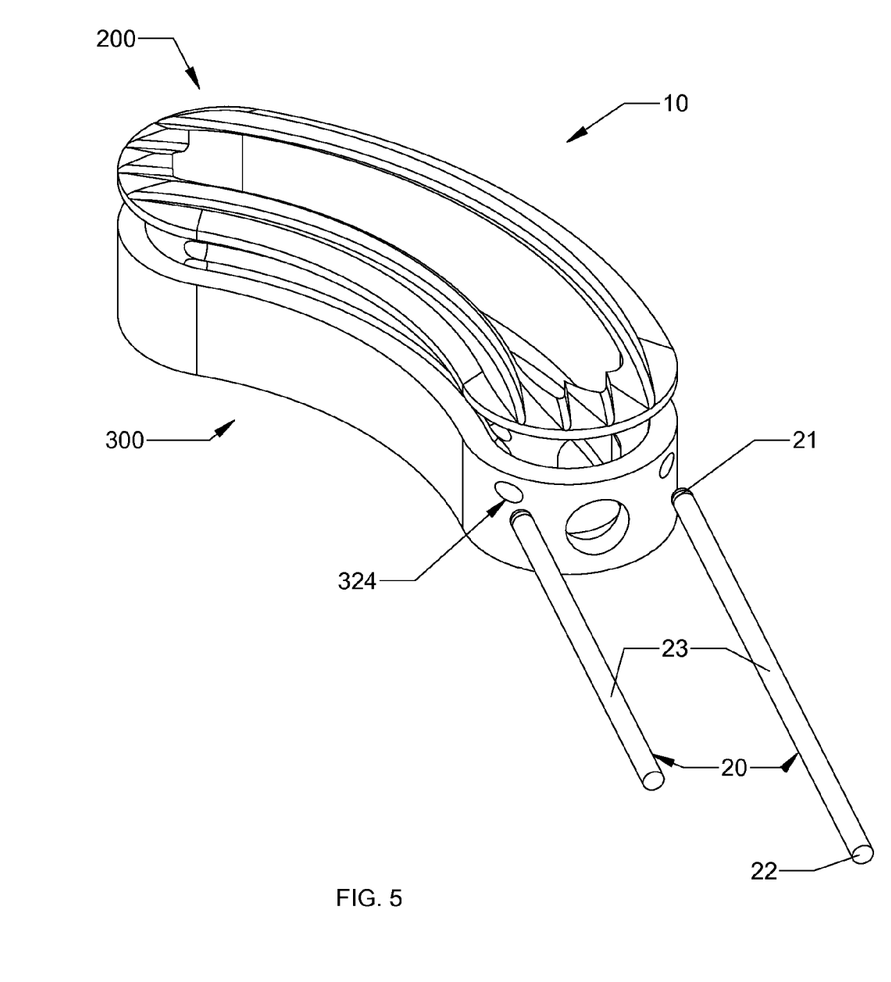
FIG. 5 is a perspective view of the expandable spinal implant of FIG. 2, shown with locking wires being inserted.
Figure 6:
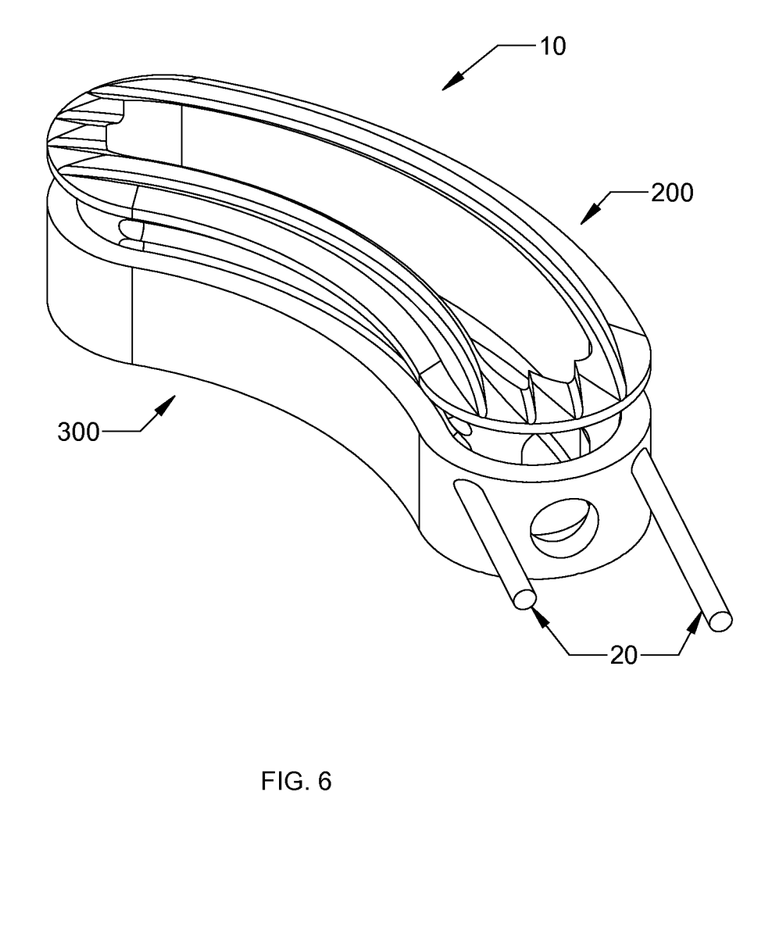
FIG. 6 is a perspective view of the expandable spinal implant of FIG. 5, shown with the locking wires partially inserted.

Referring now to the drawings, FIG. 1 illustrates an embodiment of expandable spinal implant 10 provided in accordance with the present disclosure. Expandable spinal implant 10 includes an upper body 200, a lower body 300, and locking wires or pins 20 (FIG. 5). Upper and lower bodies 200, 300 cooperate to define a two part expandable spinal implant configured for positioning between adjacent vertebral bodies. Each of these components, along with the assembly and insertion of expandable spinal implant 10 into the intervertebral space, as well as the expansion/contraction of expandable spinal implant 10 within the intervertebral space, will be described in turn hereinbelow.

The various components of expandable spinal implant 10, or portions thereof, may be formed from various similar or different materials, depending on a particular purpose. In particular, upper and lower bodies 200, 300 may be formed from a metallic material (e.g., titanium, titanium alloy, or cobalt chrome (CoCr)) or a non-metallic material (e.g., polymeric materials such as polyetheretherketone (PEEK), nylon, absorbable polymers such as polyglycolides, polylactides, polycaprolactone, etc., ceramics, or organic materials such as bone). Locking wire 20 may be formed from titanium, titanium alloy, CoCr, or other suitable metal or polymeric material compatible with upper and lower bodies 200, 300.

With reference to FIGS. 1-3 and 7B, upper body 200 is illustrated generally as having an arcuate, kidney shape; however, it is contemplated that upper body 200 may include other shapes, such as square, rectangular, circular, oval, or the like. Upper body 200 includes an arcuate, first exterior end surface 204, at a distal or leading end 202, and a second exterior end surface 208, having a corresponding arcuate profile to first exterior end surface 204, opposite thereto at a proximal or trailing end 206. It is contemplated that first and second exterior end surfaces 204, 208 may include other, non-corresponding combinations of profiles, such as arcuate and planar, planar and arcuate, and the like. Upper body 200 extends between the first and second exterior end surfaces 204, 208 to define respective top and bottom surfaces 210 and 212 (FIG. 2-3), respectively, as well as opposed side surfaces 214, 216. Top and bottom surfaces 210, 212 are substantially parallel to each other and upper surface 210 is substantially contoured in shape; however, it is contemplated that upper surface 210 may be planar, convex, or the like, and top surface 210 and bottom surface 212 may be angled relative to each other and define an amount of lordosis. Opposed side surfaces 214, 216 are illustrated as being curved, forming rounded sides; however, it is contemplated that opposed side surfaces 214, 216 may be planar. Cut-out 218 is defined through top and bottom surfaces 210, 212. Although shown as generally having a complimentary shape to that of body 200, it is contemplated that cut-out 218 may have any suitable shape, such as square, oval, circular, or the like. It is further contemplated that cut-out 218 may be formed of a plurality of cut-outs, each having identical size and/or configuration or differing size and/or configuration.

Figure 2:
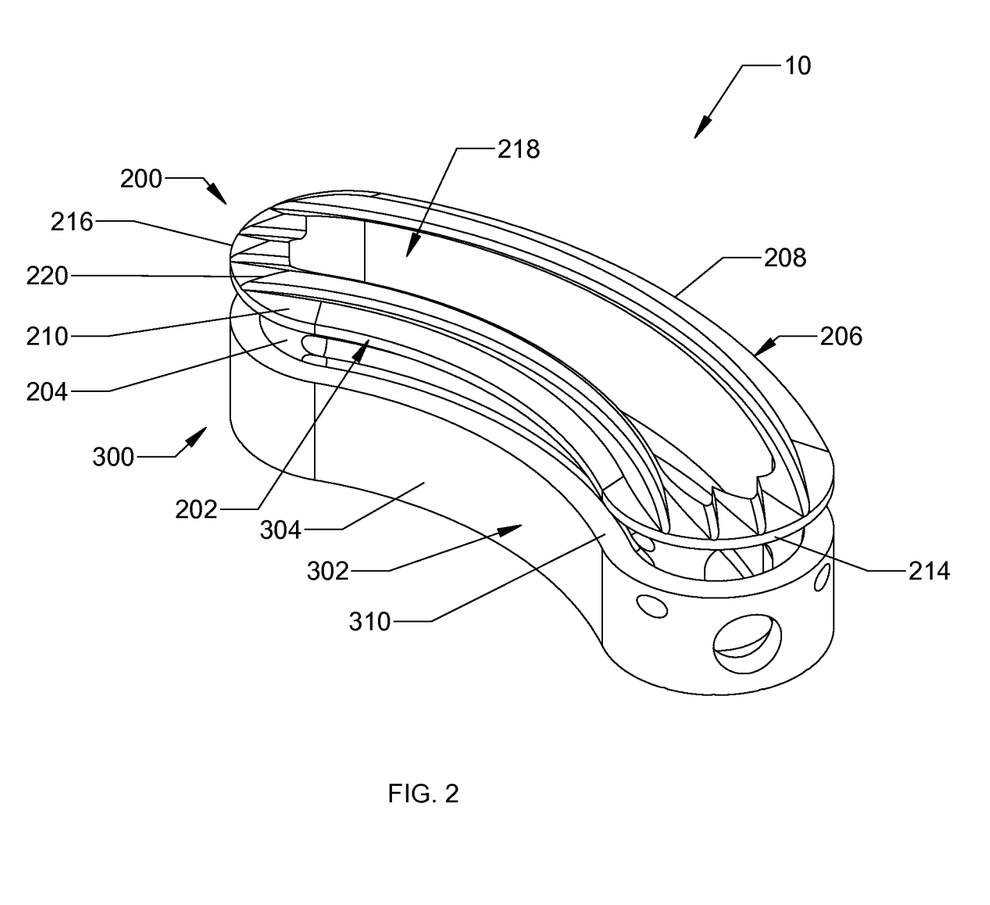
FIG. 2 is a perspective view of the expandable spinal implant of FIG. 1, shown in an expanded state.

With reference to FIG. 2, top surface 210 defines a plurality of ridges 220 arranged thereon. Ridges 220 are configured to frictionally engage an adjacent surface of a vertebral body (i.e., a vertebral endplate) to inhibit expandable spinal implant 10 from backing out of the intervertebral space since the ridges 220 will bite into the adjacent vertebral endplate.

Figure 3:
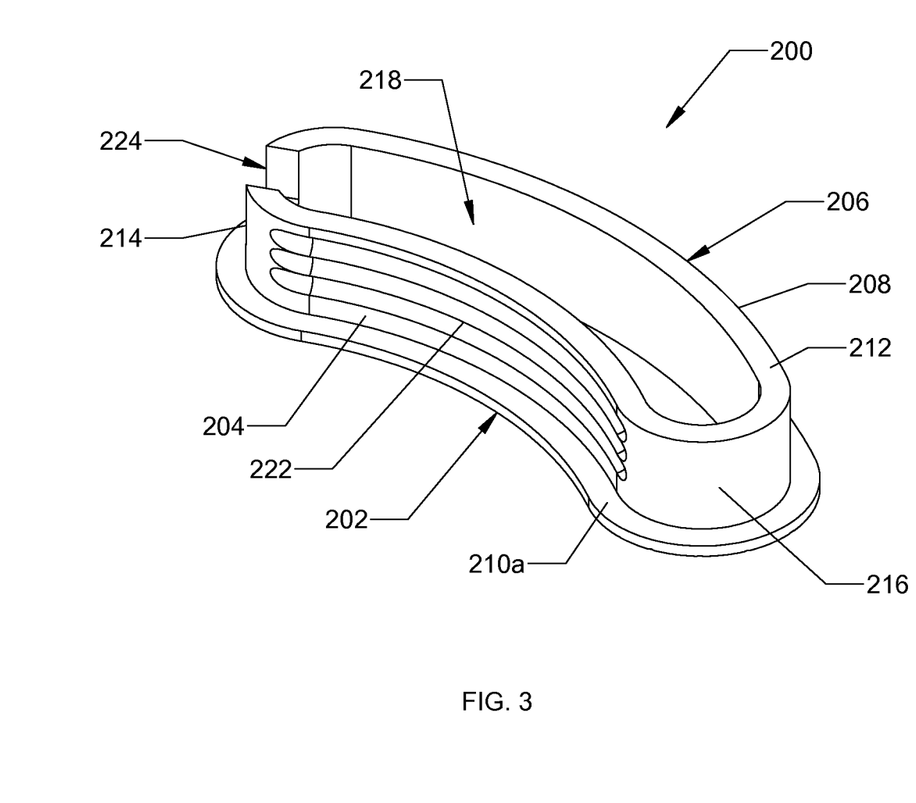
FIG. 3 is a bottom, perspective view of an upper body of the expandable spinal implant of FIG. 1.

As illustrated in FIG. 3, top surface 210 defines a flange 210a configured and/or dimensioned to abut top surface 310 (FIG. 2) of lower body 300, thereby inhibiting upper body 200 from passing entirely through bore 318 (FIG. 4) of lower body 300. First and second exterior end surfaces 204, 208 define a plurality of grooves 222 therein, extending between opposed side surfaces 214, 216. Grooves 222 are arranged on first and second exterior end surfaces 204, 208 in a stacked configuration (i.e., in a direction extending from top surface 210 towards bottom surface 212) and are configured and/or dimensioned to receive at least a portion of locking wire 20 (FIG. 5) such that upper body 200 may be extended incrementally and fixed relative to lower body 300 when locking wire 20 is advanced therein, thereby defining a height of expandable spinal implant 10. The number and size of grooves 222 arranged in a stacked configuration on first and second exterior end surfaces 204, 208 enables finer or coarser adjustment of the height of expandable spinal implant 10 within the intervertebral space.

Referring back to FIGS. 2 and 3, side surface 214 defines a slot 224 therethough having arcuate walls and extending from top surface 210 towards bottom surface 212 with an opening at bottom surface 212; however, it is contemplated that slot 224 may have other suitable shapes, such as rectangular, square, circular, or the like. Slot 224 is configured and/or dimensioned to slidably engage a suitable insertion instrument (not shown), capable of inserting and expanding expandable spinal implant 10 within the intervertebral space.

Figure 4:
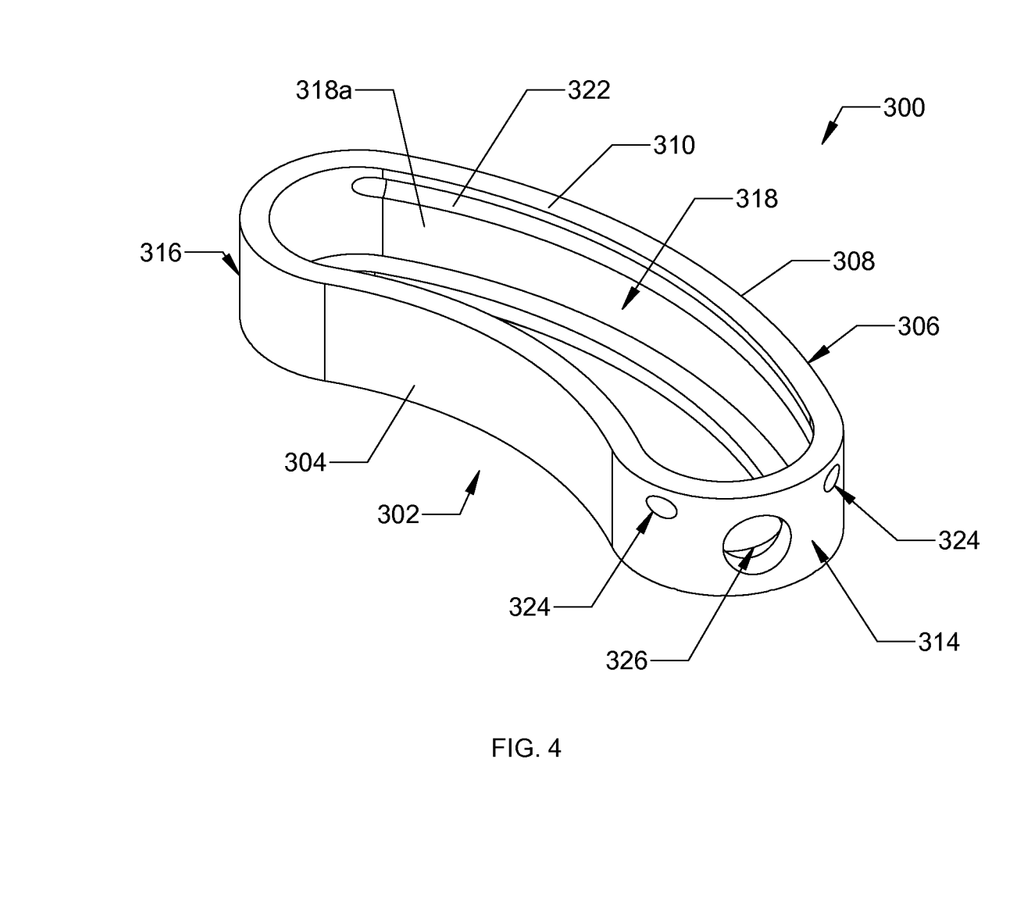
FIG. 4 is a top, perspective view of a lower body of the expandable spinal implant of FIG. 1.

Referring now to FIGS. 1, and 4, an illustration of lower body 300 is shown. Although lower body 300 is generally shown as having a shape complimentary to that of upper body 200, it is contemplated that lower body 300 may include any suitable shape, such as oval, rectangular, or the like. Lower body 300 includes arcuate, first end surface 304, at a distal or leading end 302, and a second end surface 308, having a corresponding arcuate profile to first end surface 304, opposite thereto at a proximal or trailing end 306. It is contemplated that first and second end surfaces 304, 308 may include other, non-corresponding combinations of profiles, such as arcuate and planar, planar and arcuate, and the like. Lower body 300 extends between the first and second end surfaces 304, 308 to define respective top and bottom surfaces 310, 312, as well as opposed side surfaces 314, 316. Top and bottom surfaces 310, 312 are substantially parallel to each other and bottom surface 312 is substantially contoured in shape; however, it is contemplated that bottom surface 312 may be planar, convex, or the like, and bottom surface 312 and top surface 310 may be angled relative to each other and define an amount of lordosis. Top surface 310 is complimentary to that of flange 210a of upper body 200 (FIG. 3), such that top surface 310 abuts flange 210a thereby preventing upper body 200 from advancing entirely therethrough. Opposed side surfaces 314, 316 are illustrated as being curved, forming rounded sides; however, it is contemplated that opposed side surfaces 314, 316 may be planar. Although shown as having an outer dimension equal to that of upper body 200, lower body 300 may include any suitable outer dimension that may be greater or less than that of upper body 200 (i.e., may extend beyond the outer perimeter of upper body 200, or be recessed from the outer perimeter of upper body 200).

With reference to FIG. 4, bore 318 is defined through top and bottom surfaces 310, 312, defining inner surface 318a therein. Bore 318 is configured and/or dimensioned to slidably receive upper body 200. Inner surface 318a defines grooves 322, each of the grooves 322 is disposed adjacent to distal or leading end 302 and proximal or trailing end 306, respectively, extending between opposed side surfaces 314, 316. Grooves 322 are disposed on inner surface 318a such that they are adjacent to and complimentary to grooves 222 of upper body 200 (FIG. 3), and are configured and/or dimensioned to receive at least a portion of locking wire 20 such that upper body 200 may be extended incrementally and fixed relative to lower body 300 when locking wire 20 is advanced within grooves 322 and 222, thereby defining a height of expandable spinal implant 10. As noted above, the number or size of grooves 222 arranged in a stacked configuration on first and second exterior end surfaces 204, 208 enables finer or coarser adjustment of the height of expandable spinal implant 10 within the intervertebral space as locking wire 20 is advanced within apertures 314 (FIG. 1), grooves 322, and the selected grooves 222 of upper body 200.

Referring back to FIG. 1, side surface 314 defines apertures 324. Apertures 324 extend through side surface 314 and inner surface 318a of bore 318 (adjacent to side surface 314), such that apertures 324 are coaxial with grooves 322, thereby permitting locking wire 20 to be fully advanced therein. Through-hole 326 extends through side surface 314 and is aligned with slot 224 of upper body 200 such that a suitable insertion instrument (not shown), capable of inserting and expanding expandable spinal implant 10 within the intervertebral space, may be inserted such that lower body 300 is held stationary relative to upper body 200 while expandable spinal implant 10 is expanded, or vice versa.

Figure 7A:
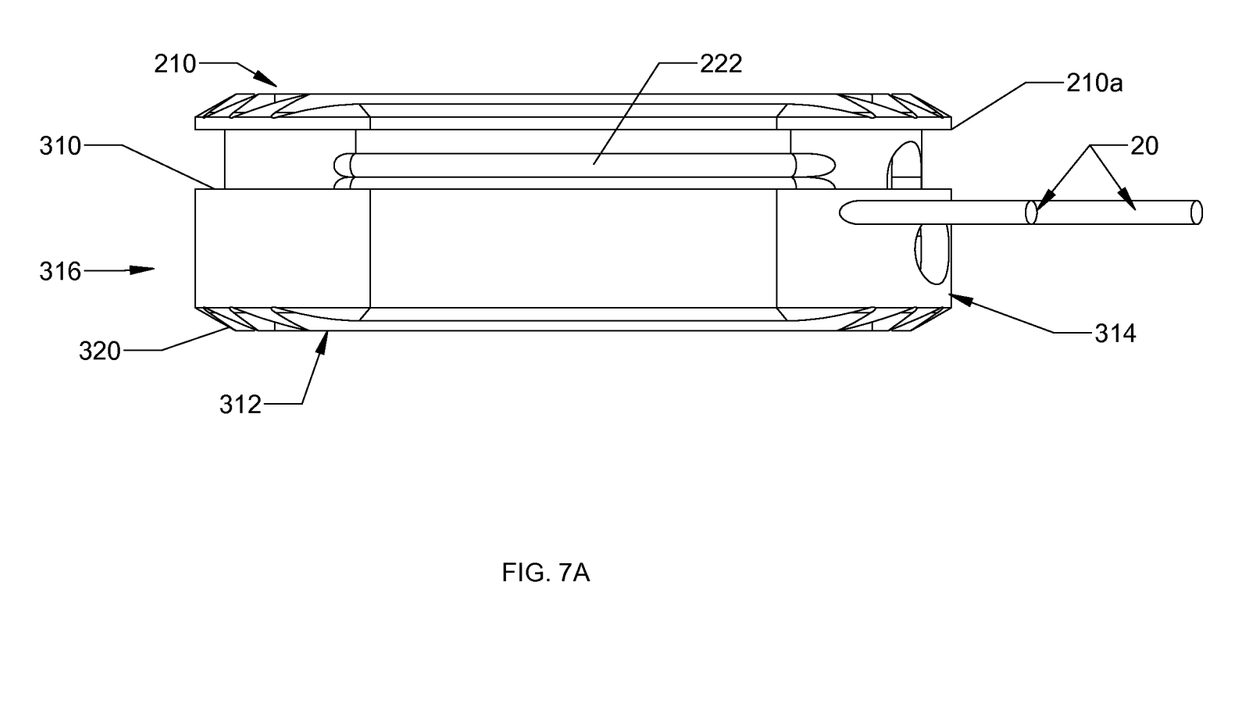
FIG. 7A is a side view of the expandable spinal implant of FIG. 6.
Figure 7B:
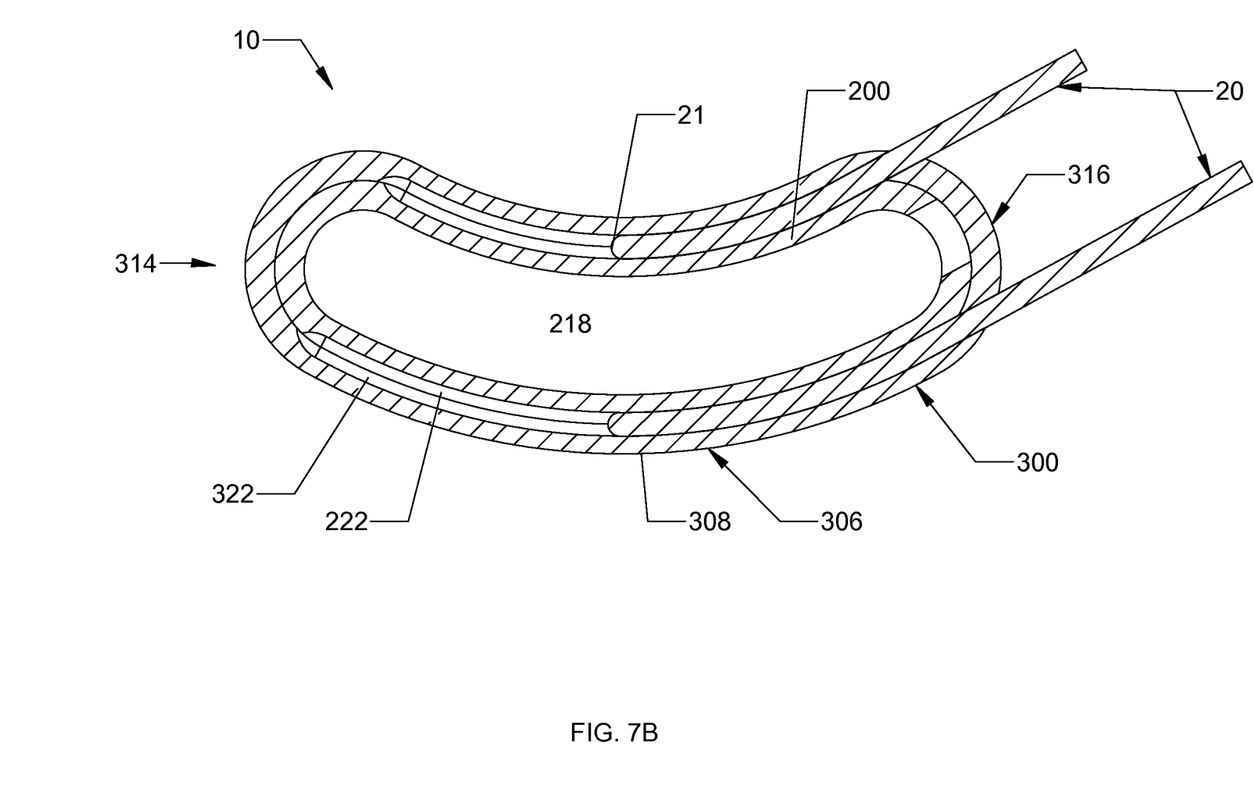
FIG. 7B is a top, cross-sectional view of the expandable spinal implant of FIG. 7A.

Referring now to FIG. 7A, bottom surface 312 defines a plurality of ridges 320 arranged thereon. Ridges 320 are configured to frictionally engage an adjacent surface of a vertebral body (i.e., a vertebral endplate) to inhibit expandable spinal implant 10 from backing out of the intervertebral space since ridges 320 will bite into the adjacent vertebral endplate.

With reference to FIGS. 3 and 5B, an illustration of locking wire or pin 20 is shown. Locking wire 20 includes first and second ends 21, 22 defining an elongate body 23 therebetween. Although first end 22 is shown generally as being planar, and second end 21 is shown generally as being rounded or blunt, it is contemplated that both first and second ends 21, 22 may be rounded or blunt. Locking wire 20 is dimensioned and/or adapted to be received within apertures 324, grooves 222, and grooves 322 such that the locking wire 20 is partially disposed in each groove 222, 322 such that frictional force between the locking wire 20 and the grooves 222, 322 prevents the upper body 200 from collapsing into lower body 300. Upper body 200 may be fixed relative to lower body 300 when locking wire 20 is fully advanced therein, thereby defining a height of expandable spinal implant 10.

With reference to FIGS. 1-7B, the insertion of an expandable spinal implant 10 into the intervertebral space during the course of a spinal surgical procedure is described. Initially, upper body 200 is advanced within bore 318 of lower body 300 such that flange 210a of upper body 200 abuts top surface 310 of lower body 300. The intervertebral space is then prepared, e.g., damaged or diseased tissue is removed. The expandable spinal implant 10 is affixed to a suitable insertion instrument (not shown) using slot 224 and through-hole 326 of upper and lower bodies 200, 300, respectively. At this point, expandable spinal implant 10 may be advanced within an incision within the patient and thereafter, a previously prepared intervertebral space of the patient's spine. The insertion instrument is then manipulated to expand expandable spinal implant 10 to a desired location such that a pair of grooves 222 of upper body 200 align with grooves 322 of lower body 300. Expansion of expandable spinal implant 10 is effectuated by advancing upper body 200 axially in bore 318 of lower body 300, which adjusts the height of expandable spinal implant 10. This height adjustment may be performed by various means including a scissor jack, hydraulic mechanism, or other such device. Alternatively, expandable spinal implant 10 may be manually expanded prior to insertion of locking wires 20. The desired location of upper body 200 relative to lower body 300 is selected based on the desired height of expandable spinal implant 10. Once a desired location has been selected, locking wires 20 are advanced within apertures 324, grooves 222, and grooves 322 such that the locking wire 20 is disposed partially in grooves 222, 322 to lock the position such that the upper body 200 may be fixed relative to lower body 300 when locking wires 20 are fully advanced therein. Once the desired location is fixed, the insertion instrument may be released from expandable spinal implant 10 and removed from the incision. Lastly, the interior space of cut-out 218 of upper body 200 may be packed with bone in-growth material, drugs, or other suitable materials or compounds.

This process may be repeated as many times as the procedure requires, whether it be for the same expandable spinal implant 10 or for a plurality of expandable spinal implants 10 as required by the procedure being performed.

It will be understood that various modifications may be made to the embodiments of the presently disclosed expandable spinal implant. Therefore, the above description should not be construed as limiting, but merely as exemplifications of embodiments. Those skilled in the art will envision other modifications within the scope and spirit of the present disclosure Expandable spinal implant 10 may be inserted using a variety of surgical techniques, including but not limited to, an anterior approach, an anteriolateral approach, a lateral approach, a retro-peritoneal approach, or a posterior approach. Expandable spinal implant 10 is usable in a number of procedures including Anterior Lumbar Interbody Fusion (ALIF), Posterior Lumbar Interbody Fusion (PLIF), and Transforaminal Lumbar Interbody Fusion (TLIF).

What is claimed is:

1. A spinal implant, comprising:
    an upper body having an outer surface adapted to engage a first vertebral body, the upper body defining an arcuate profile extending between opposed end surfaces, the upper body defining opposed side surfaces having a concave profile and a convex profile respectively;
    a cavity defined through the outer surface and an opposing surface of the upper body;
    grooves disposed on each side surface of the opposed side surfaces of the upper body, the grooves extending along, and conforming to, the arcuate profile of the upper body;
    a lower body having an outer surface adapted to engage a second, opposing, vertebral body, the lower body having a bore to slidably receive a portion of the upper body, the bore having grooves disposed on opposing sides of an inner surface of the bore;
    a hole defined through a side surface of the lower body, the hole configured to engage an insertion instrument capable of inserting the spinal implant between adjacent vertebral bodies;
    a slot defined through a side surface of the upper body and an opposing inner surface defined by the cavity of the upper body, the slot configured to slidably engage the insertion instrument such that the upper body may advance axially in the bore of the lower body;
    first and second apertures extending through an end surface of the lower body; and
    first and second pins adapted to be received within the first and second apertures, grooves of the lower body, and the grooves of the upper body to enable the first and second pins to fix a position of the upper body relative to the lower body, wherein the first and second pins are adapted to deform to the arcuate profile of the upper body as the first and second pins are advanced within the grooves of the upper body.

2. The spinal implant of claim 1, wherein the outer surfaces of each of the upper body and the lower body include ridges adapted to engage the first and second vertebral bodies.

3. The spinal implant of claim 1, wherein the grooves of the upper body are disposed in a stacked orientation.

4. The spinal implant of claim 1, wherein the upper body includes a flange disposed on the outer surface adapted to abut the opposing surface of the lower body.

5. The spinal implant of claim 1, wherein the first and second pins are constructed of a flexible material, such that the first and second pins may deform to the arcuate profile.

6. The spinal implant of claim 1, wherein the lower body defines an arcuate profile extending between opposed end surfaces, the lower body defining opposed side surfaces having a concave profile and a convex profile respectively.

7. The spinal implant of claim 6, wherein the bore of the lower body includes an accurate profile corresponding to the arcuate profile of the upper body.

8. The spinal implant of claim 7, wherein the grooves of the bore of the lower body include a corresponding accurate profile.

9. The spinal implant of claim 1, wherein the outer surface of the upper body is parallel to the outer surface of the lower body.

10. The spinal implant of claim 1, wherein the outer surface of upper body defines a first plane and the outer surface of the lower body defines a second plane, wherein the first plane is parallel to the second plane.

* * * * *